Figure 1:
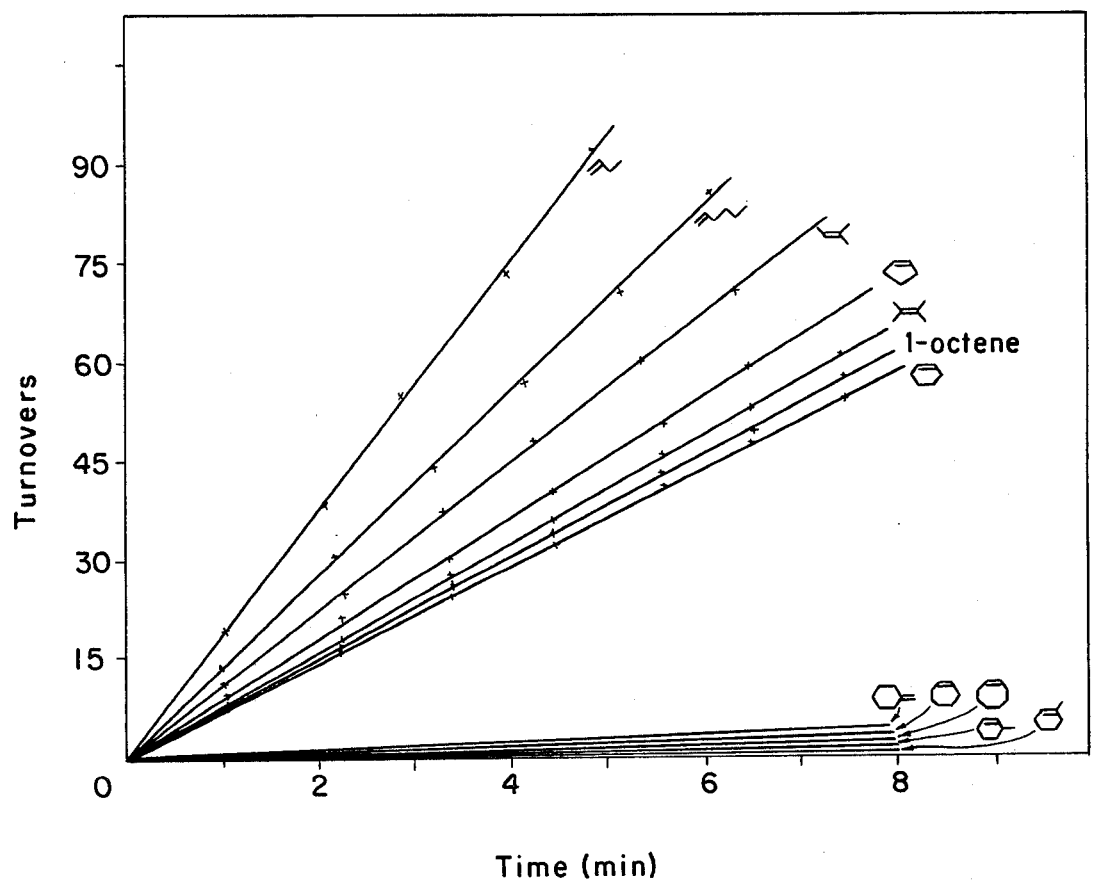

United States Patent [19]

Schwartz et al.

[11] 4,444,898

[45] Apr. 24, 1984

[54] HETEROCATALYST SYSTEM

[75] Inventors: Jeffrey Schwartz, Princeton, N.J.; Tai-Nang Huang, New Haven, Conn.

[73] Assignee: University Patents, Inc., Norwalk, Conn.

[21] Appl. No.: 336,821

[22] Filed: Jan. 7, 1982

[51] Int. Cl.³ .............................................. B01J 29/10
[52] U.S. Cl. ......................................... 502/62; 502/74
[58] Field of Search ................... 252/455 Z, 431 R; 502/62

[56] References Cited

PUBLICATIONS

Metal–Zeolite Catalysts, Minachev et al., Zeolite Chemistry and Catalysis by Jule A. Rabo, ACS, Wash., D.C. 1976, pp. 556–558.

Primary Examiner—Carl F. Dees
Attorney, Agent, or Firm—Fred A. Keire

[57] ABSTRACT

Heterocatalyst systems wherein a metal complex is reacted with an —OH group that is in a zeolite or molecular sieve pore, aperture, channel, cavity or cage; improved carbonylation and hydrogenation catalysts, as well as catalysts for Fischer-Tropsch reactions are disclosed; rhodium reaction product with an —OH group within a type 13X or 13Y zeolite cage is a typical catalyst.

45 Claims, 2 Drawing Figures

The rate of hydrogenation of olefins catalyzed by (Z-X)-ORh(allyl)H
Conditions: Catalyst (50 mg, 0.01 mmol Rh); (olefin)=0.2 M in hexane; $H_2$ (1 atm); 20°C

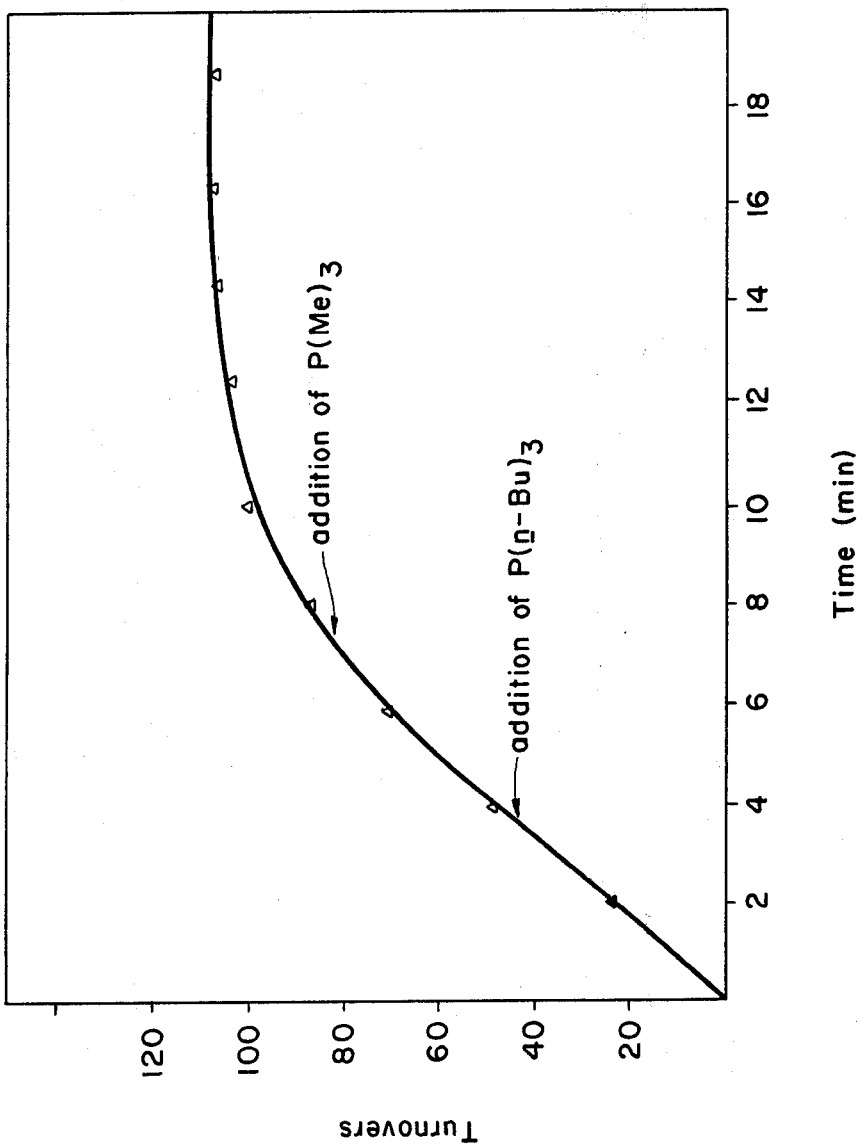

HETEROCATALYST SYSTEM

This invention relates to catalysis; more specifically, this invention relates to a heterocatalyst system where the catalytic result stems from two catalyst types, a metal part and the metal reacted with another catalytically active or even inactive substance. However, the contribution to catalysis is vastly improved by the metal catalyst co-acting with the other substance acting catalytically. Thus, the combination of the two far surpasses the individual catalysis action of either or shows activity where no individual catalysis action is found for one or both of the catalyst species.

Particularly, this invention pertains to metals deposited within the pores or cavities of zeolites in a very specific manner so as to derive the catalytic activity not only from the metal, e.g. a Group VIII metal, but also from the zeolite structure. Thus, this invention is directed to selective activation of zeolites under fairly mild conditions such as ambient, and yet forming stable compounds therewith having excellent properties. As a result, thermally induced migration, if not entirely eliminated, is substantially minimized. Hence, repeatable, predictable and controlled catalysis is now possible. Still further, this invention pertains to a method of depositing the Group VIII metals within the pores or the cages of the zeolite to obtain novel catalyst materials and the application of the novel catalysts for improving reactions such as hydrogenation, carbonylation, Fischer-Tropsch, etc. Further, this invention provides catalysts of tailored activity by selectively enhancing the catalytic activity of the metal deposited within the pore or cage structure of the zeolites. Still further, this invention pertains to stage-wise hydration and hydrogenation and thus activity of different zeolite and other support bound metals acting as catalysts for hydrogenation. Hence, the intermediate stage catalysts are within the scope of the invention, as well as methods for characterizing the catalyst product so as to distinguish the desirable from the undesirable product and to "clean-up" the unwanted depositions.

BACKGROUND OF THE INVENTION

In the use of zeolites as molecular sieves and catalyst supports, a great effort has been made to improve selectively the activity of these catalysts by devising a heterocatalyst system with the zeolite acting as a catalyst and a metal deposited on or reacted (in the formation of the zeolite) therewith, thus due to its molecular sieve function further enhancing the catalytic activity of the zeolite. This invention, however, pertains to the selective activity of the heterocatalyst system wherein the metal is deposited, i.e. reacted, within the pores or the cage of the zeolite in a specific replacement by a metal complex. This invention, therefore, must be distinguished from the, in gross, modification of the zeolite systems incorporating metals in these in a random fashion or in the production of these zeolites or by subsequent exchange or ion replacement, in gross and other methods disclosed in the art.

In the art of zeolite chemistry, a number of conventions have been adopted for characterizing the molecular sieve zeolites. For purposes of the present invention, the molecular sieve zeolites will be defined by the terminology found in *Experimental Methods in Catalytic Research*, Volume 2, "Preparation and Examination of Practical Catalysts", Chapter 1 authored by A. P. Bolton, and entitled "Molecular Sieve Zeolites", Academic Press, Inc., (1976), and includes from Table I therein the suitable zeolites as further defined below, i.e. Type X, Y, Mordenite, L, Erionite, and Zeolite Ω, but any other structure formed by other arrangements in pores, apertures, or cages is intended as long as appropriate dimensions are met, either for the metal complex or the zeolite structure.

BRIEF DESCRIPTION OF THE PRIOR ART

With respect to the prior art for homogeneous catalysis, for a Group VIII metal, the rhodium catalysts disclosed in U.S. Pat. No. 3,769,329 to Paulik et al., issued Oct. 30, 1973, are representative. With respect to the description of the prior art zeolites, those found in the Linde "catalyst" brochures under the "Linde Molecular Sieves Catalyst Bulletins" are illustrative of the zeolites; further illustrations will be given below.

With respect to the metals which have been reacted with a support, the disclosure found in the report by I. R. Leith entitled *Hydrogenation and Fischer-Tropsch Synthesis on Zeolite-Supported Group VIII Metal Catalysts* appearing in Chemical Engineering Research Group publication of the Council for Scientific and Industrial Research, Pretoria, South Africa, November 1977, is pertinent (hereafter CSIR Report CNG 218). The disclosure in this publication pertaining to the introduction of a metal via an organometallic compound which reacts with the zeolitic hydroxyl groups is found in Section 4.1 under the heading "Metal-Loaded Zeolites." However, the disclosure in this report fails to differentiate, and, in fact, relates merely to in gross distribution of metal without the recognition of the heterocatalyst system which is a reactant between the metal and the zeolite and only in an aperture or a cell cavity thereof. The references mentioned in this report are also relevant.

Further, in the search for prior art, applicant has also noted the following references which may be of interest. Weisz et al., *J. Catal.*, Vol 1, pp. 307 et seq. (1962). This reference describes incorporation, in gross, of a metal in the zeolite structure during the zeolite structure forming process. Mantovani et al., *J. Molec. Catal.*, Vol. 3, pp. 285–291 (1977/78). It seems fairly certain that zeolite treated with a metal complex did not result in a reaction product, but rather an exchange or absorption in a random manner. Further references which are illustrative of undifferentiated deposition, such as by exchange of rhodium complexes with zeolites, are Scurrell et al., *J. Mol. Catal.*, Vol. 7, pp. 535 et seq. (1980) and Vol. 10, pp. 57 et seq. (1981); Yamanis et al., *J. Catal.*, Vol. 69, pp. 498 et seq. (1981) is also a reference of interest in this connection.

It is, however, evident that none of these references discloses a heterocatalyst system of the type described and claimed herein.

DESCRIPTION OF THE INVENTION

In accordance with the present invention, it has now been found that metals with proper substituents and of proper size can be introduced into the pores, apertures, and channels, as well as into the cage of zeolites and reacted therewith, and provide heterocatalyst systems of outstanding properties.

The method for introduction of these organometallic compounds comprises not only the proper preparation of the introduced metallic compound with pre-selected substituents thereon, but also the reaction of this organometallic compound within the zeolite pores, apertures, channels or the cages so as to form a proper reactant with the zeolite within the same. In addition to reacting within the pores, or the apertures, or the cage, the reaction is also fruitfully carried out further and allowed to take place on the outside of the zeolite to provide perhaps two-or three-metal systems which react with a reactant stream generated in situ or of different compositions, which streams thereafter can be readily separated by conventional separation means, e.g. distillation or fractionation, molecular sieves, etc. For example, a stream of hydrogen, methanol, and carbon monoxide catalyzed by the herein described rhodium complex results in methyl acetate which thereafter (or conjointly with a fresh co-fed stream of methyl acetate) reacts with ruthenium catalyst (formed of a very susceptible, i.e. to protonation, complex of ruthenium) which has been reacted with the outside (—OH groups, etc.) of the zeolite to produce ethanol and methanol. Thus, within the scope of this invention is an appropriate "back" poisoning of the "outside", or further ligand formation on the "outside" of the zeolite which is then usefully employed, as illustrated above. Still further, as part of the inventive method, it has been shown that "clean up" of the outside of the zeolite is possible by a reaction with a catalytic poison of a size that cannot enter the apertures or the cage, but yet can clean up the outside of the zeolite sites with which the metal may have accidentally reacted. Hence, not only the preparation of the proper zeolite metal reaction, but also the introduction or modifications or different reactions where mixed streams in tandem or in seriatim are being treated are illustrated, including the improvement in the overall efficiency of the zeolite catalyst combination. These combinations are based on different protonation susceptibility of different metal complexes vis-a-vis the "active" zeolite sites.

In the attached drawings various aspects of the invention are illustrated and wherein:

FIG. 1 shows the rate of hydrogenation of unsaturated compounds as a function of their size, and FIG. 2 illustrates the effect on rate of hydrogenation by the addition of catalytic poisons of different sizes.

Inasmuch as the present invention comprises, first, a size-dependent reaction of the metal within the zeolite, this invention includes as a function of the overall reaction scheme the cage size and/or the pore openings, as well as the zeolite or molecular sieve hydroxy ion activity within the pore openings or within the cage.

Further, this invention includes as a function of the catalytic activity of the newly formed zeolite-metal combination, other considerations such as the entry size of the reactants, the reaction product species size, the exit size of the reactants, etc. Thus, the residual space left in the cage or pore after binding of the zeolite with the metal must be taken into consideration as part of the reaction, or in the marginal conditions as part of the reaction rate.

Still further, although quantitatively subject to less precise definition, the substrate acidity or protonation ability must be such that the zeolite ions can be exchanged by removing from the substrate thereof sodium, potassium and introducing therefor a proton. This may be accomplished such as by ammonium exchange. If differentiated metal introduction is sought, then it is accomplished by other exchanges where sodium or potassium has been exchanged by means of tributyl ammonium salts or triethyl ammonium salts outside the zeolite surface and then ammonium exchanged for inside the zeolite cage.

Within the inventive concept partially hydrogenated or hydrated metal-zeolite catalysts are included. These partially hydrogenated and hydrated metal-zeolite catalysts allow hydrogenation of various species of unsaturated compounds at different rates, and thus provide tailor-made (within the cage or within the pore) deposited zeolite-metal-metal substituent combinations which allow reactions to proceed at specific conditions, thereby greatly facilitating the selection of a proper, tailor-made catalyst to answer specific and needed catalysis conditions. This mild activation of the catalyst, therefore, is very useful. In the event of the zeolite-metal-metal substituent reaction with carbon monoxide, the reaction species, e.g. carbonyl, of course, differs from the partially hydrogenated, for example, alkyl, allylic, alkenyl, alkynyl or aryl substituent metal-zeolite reaction product, and thus this catalyst is suitable again for a different purpose or at different activity levels. Typically, of the above substituents up to four carbon atoms may safely be employed for the non-aryl species, but when mixed substituents are used, a smaller size of some, in a mixed substituent complex, allows larger substituents for others, e.g. up to octyl or octenyl, as long as these are straight chains. For aryl substituents, phenyl with at most one or two substituents on the phenyl ring are useful. In any event, the zeolite pore, aperture, or channel openings will govern the eventual size and is, therefore, the final test. An illustrative aryl compound is triphenyl chromium.

Of the zeolites and the structures thereof which are within the scope of this invention, there are included the large pore zeolites known as type X, Y, L, Omega, Erionite, Mordenite and various modifications thereof. Further, amongst the modifications are the crystalline silicalite having uniform pore dimensions such as disclosed in U.S. Pat. No. 4,061,724. Further, catalysts of the type described in British Pat. No. 1,178,186, known in the trade as ELZ-$\Omega$-5 and ELZ-$\Omega$-6, available from Union Carbide Corporation and those also described in Union Carbide Molecular Sieves Developmental Product Brochures, ELZ-E-5E-6E-8E-10 are included. For purposes of illustration, the materials described therein are incorporated herein by reference. These broadly defined "zeolites" or molecular sieves are available in the trade from various other sources and are described in the trade literature, and the above references are merely for the purpose of convenient exemplification.

In general, the preferred group of the zeolites are the type X, Y, L and Omega, with the requisite zeolite acidity (for a reaction with the metal complex) being obtained by ion exchange and thermolytic treatment of the same, or being inherent in the product available as such. The requisite acidity is obtained such as by ammonium exchange, so that at least one metal can be reacted per cell or pore with the acidic hydroxyl group within the cell or the pore and that at least one mono-metal or two bi-metal atoms per cell cavity can be obtained as reactants with the zeolite.

Still further, of the various types of zeolites, the protonated type X and Y, specifically 10X and 10Y and 13X and 13Y type, as it is well known in the art, have a cage dimension of sufficient size and a pore diameter of size corresponding thereto, such as of about 7.5 angstroms, and for this reason are the preferred species. The aperture, or entering port dimensions, is the limiting condition for the complex entry, but for a reaction catalyzed by these zeolites, the leaving product molecule may also define the catalytic activity. The molecule by which the metal sought to be deposited is being introduced is the smallest organic substituent carrying a molecule of the metal complex. These metal complexes must enter the aperture and be reacted within it or the cage. The reaction takes places within these and the zeolite due to the different acidity of the hydroxyl groups within the aperture or within the cage. Although the pore or aperture size is temperature influenced, for practical purposes the respective reaction temperature(s) will be governing.

With reference to a specific metal, the disclosure herein has emphasized the zeolite-rhodium metal combination with various degrees of rhodium metal substitution, for example by alkyl, allylic, alkenyl or aryl species, or mixtures of same, within the cage or pore of the zeolite. Other metals of Group VIII are exemplified, such as cobalt. Further, protolytically labile metal complexes of other metals such as zirconium, niobium, vanadium, tantalum, hafnium, molybdenum, rhenium, titanium, chromium, tungsten, manganese, palladium, platinum, ruthenium, nickel, osmium, iridium, iron, copper, etc., are within the contemplation of this invention in view of the formation of the zeolite-metal reaction within the pores or the cages of the zeolite by these protolytically labile ligands with the acidic hydroxyl group. Of the above group, Group VIII metals are desired; of these, cobalt, nickel, rhodium, palladium and platinum form the highly desired group of which, in turn, cobalt and rhodium are foremost in consideration. Rhodium is the preferred species. The various organometallic species which are available for these of the size capable of being introduced and reacted within the pore aperture or cavity of the zeolite (and still allowing the various reactions to take place therein) are included within this invention.

In addition, and as evidenced from the experience with the zeolite-rhodium heterocatalyst system, the reactions with the heterocatalyst system are at least as efficient as with the homogeneous catalyst systems, with great benefits associated with the ready separation of the heterocatalyst system from the reaction medium. In some cases, such as in the Fischer-Tropsch reactions, and carbonylation, the reactions are vastly and outstandingly better so as to give rise to synergistic results heretofore not appreciated in the catalyst art. For example, the carbonylation of methanol catalyzed homogeneously by rhodium complexes and the attempts to develop heterogeneous analogues of this process have been reported, but the rates for conversion of methanol reported for non-soluble catalyst systems investigated are far lower than those found for homogeneous analogues. These reports have included supports for the metal, such as polymers, active carbon, alumina, and several zeolite supports. In fact, the use of some supports, such as silica and magnesium oxide, has been noted to give rise to inactive carbonylation catalyst systems.

While it has been reported that the catalyst system prepared by ion exchange between sodium type X-13X zeolites with [Rh(NH$_3$)$_5$Cl] Cl$_2$ is far more reactive for methanol carbonylation than is the analogue prepared by ion exchange with RhCl$_3$, it is surprising, indeed, that the very specific location and distribution of the rhodium species achieved within this solid material has such a significant and outstandingly beneficial result in controlling catalytic activity as achieved by the present invention.

As a result of the above invention, it has now been found that specifically deposited catalyst systems display very high turnover rates (defined as mole product/mole catalyst/hour) and selectivities (defined as percent desired material/all products obtained) for methanol carbonylation which are comparable at least to those of the well-known homogeneous species or far superior to the heretofore studied supported species, and outstandingly better for various other reactions heretofore catalyzed by various other reactants not specifically placed, not specifically reacted, or not specifically substituted on the zeolite.

In the carbonylation reaction, methyl iodide is used. As now found, the ability to use a very low ratio of methyl iodide to methanol is advantageous compared with other processes which normally require methanol to methyl iodide ratios of 8 to 15:1.

In the reactions described herein, carbonylation requires the oxidative addition of $CH_3$—X, where X is halogeno, i.e. iodo, bromo, chloro, and more remotely fluoro moiety, to a rhodium (I) carbonyl species which are obtained when the zeolite-bound rhodium has been reacted with carbon monoxide. A reaction product is methyl acetate and a promoter is typically an iodide. The effectively unsaturated nature of these oxide-bound Rh(I) carbonyls may be responsible for the high rates that these display for $CH_3$—X activation. This reaction is in distinction, rate-wise, from the silica and alumina supported analogues of the rhodium carbonyl and is believed to be attributable to a support-substrate interaction which exists inside the zeolite cage or pore environment. Thus it is believed that the departure of the halide in a displacement reaction may be facilitated by the interaction between the leaving group and the Lewis acidic sites of the zeolite cage or pore structure.

This is inferred, because substrates, as otherwise unreactive toward carbonylation as methyl chloride, can be carbonylated in the presence of methanol using the herein disclosed rhodium complexes bound in the zeolite cage, but also bound to Lewis acidic supports, such as, for example, [Al]—ORh(CO)$_2$, [Si]O—Rh(CO)$_2$, etc., which are improved on the basis of temperature, turnover rate, pressure of carbon monoxide, etc. for some specific reactions, as further disclosed herein. Hence, improvements in catalysis using aluminum oxide and other supports are also within the scope of the invention for some specific reactions. However, complexes of the herein disclosed metals on Al$_2$O$_3$ or SiO$_2$ supports confirm also the superiority of the modified zeolite catalysts, because the latter are vastly more active.

Of the metal catalysts claimed, those complexes of Group VIII metals of the Periodic Table of Elements are preferred for the Al$_2$O$_3$ and SiO$_2$ supports. Of the same, rhodium is exceptionally outstanding.

In general, the protolytically labile ligands can be depicted by the following general formula: $M^nR_nL_m$, where M is a metal in any of its oxidation states and substitutable with a substituent, which may be the same or different and which correspond in number to the oxidation state of the metal. Thus, n in the formula can be from 1 to 7, the last being rhenium as an illustration. As R, a ligand of the metal is intended. L is a neutral ligand with m representing the residual number of the coordination number for the metal which needs to be satisfied. An illustration is Rh(allyl)$_3$ for Rh(III) or Ru(allyl)$_2$(olefin)$_2$ where the olefin is of two to eight carbon atoms, either straight chain or cyclic, e.g. ethylene up to 1,5 cyclooctadiene. Another illustration is Cu(allyl) (dimethyl sulfide); (Cr) (triphenyl), etc. As ligands, the organic, organophilic, and hydrophilic ligands are included. These, when substituted on the molecule, allow the entry of the metal containing molecule in the largest aperture or opening of the zeolite and allow the metal to react therein with an hydroxyl moiety of the zeolite. However, the molecule size is important. More specifically, the R substituents must be such, that in combination with the metal, the molecule can enter the desired or selected pore opening. R substituents are preferably hydrocarbyl substituents, such as alkyl, allylic, alkenyl, alkynyl, aryl, and also hydride as previously specified, and other radicals, such that the diameter of the molecule is no more than 10 Angstroms, or in any event no bigger than the entry pore, channel, or aperture for the zeolite subject to the reaction therewith.

Further, more typically and desirably the complexes are of a size of less than 7.5 Angstroms for the type X and Y zeolites, again defined above, and more typically of a size less than 7 Angstroms in diameter is desired, preferably of about 6 Angstroms. When these dimensions are given, these are the maximum dimensions that are intended at room temperature.

In order to improve the solvating ability, some of the R substituents may represent substituents having hydrophilic functions, typical of these are —OR, —CO$_2$R, —NR$_3^+$, —O$^-$, and —CO$_2^-$ where the substituents, again as size limited, are represented by the above defined R moieties. Suitable substituents and of the preferred type are alkyl, allylic, alkenyl, aryl and mixed substituents, of these from 1 to 8 carbon atoms, subject, of course, to the size limitation of the total molecule. Thus methyl, ethyl, n-propyl, allyl, ethenyl, acetylide, and phenyl are the highly desirable substituents. The metal ligands having an entire substituent configuration of allylic ligands, or at least a majority of allylic ligands, are the most desirable species of the metal compound sought to be introduced within the aperture or cavity of the zeolite.

Descriptions of these compounds are found such as in the article authored by Schrock et al. entitled "Sigma-Alkyl and -Aryl Complexes of the Group 4 to 7 Transition Metals" appearing in *Chemical Reviews*, Vol 76, No. 2, ps. 243-268 (1976), and Davidson et al., "Metal Sigma Hydrocarbyls, Etc." appearing in *Chemical Reviews*, Vol. 76, No. 2, pp. 219-242 (1976). These articles are incorporated by reference herein.

Other sources disclosing these metal complexes containing the protolytically labile ligands are found in an article authored by Wilke et al., entitled "Allyl-Transition Metal Systems" in Internat. Ed. *Angewandte Chemie*, Vol. 5, No. 2, pp. 151-266 (Feb. 1966), and Belgian Pat. No. 631,172 and which (or their counterpart patents) are incorporated by reference herein.

By the term "protolytically labile complexes", it is intended to mean the compounds which have been defined above and which will react with an acidic substrate of the zeolite or the molecular sieves of the types defined above when these have been protonated or proton exchanged, as further defined herein, and/or possess an acidity for the zeolite hydroxyl group which is at least capable of reacting with the metal complex. By acidity is meant the ability to protonate a metal complex.

As mentioned before, the allylic ligands surrounding the metal are the most desirable ones. However, these need not be the same, as there are several pathways by which an allylic ligand can be introduced into the coordination sphere of the transition metal. Thus, along the same lines, organic solvent solubility may be imparted to these complexes through the use of allylic ligands which are substituted by alkyl, aryl, alkenyl, alkynyl groups, etc. (more typically, however, alkyl and aryl groups), or by hydrogen or amino in combination therewith or by itself or by halogen group or by a carboxylic acid ester. By carboxylic acid esters are meant those which still provide the dimensions to the molecule not exceeding those specified above. Amongst these are intended to be carboxylic acid side chains from 1 to 3 number of carbon atoms with the ester function again being governed by the size definition above and being no more than from 1 to 4 carbon atoms.

In order to impart solubility in aqueous media or in mixed solvent media, it is also possible to attach solubilizing functionality to these allylic radicals taking advantage, of course, of the various allylic ligand introduction routes into the coordination sphere of the transition metal. Such units, within the contemplation of the present invention, are organo-ammonium or sulfonium salts, carboxylate salts, or carboxylic esters previously mentioned. A free amino group or an alkyl amino group may also be employed as one of the R radicals. Similarly, a hydroxyl group of an alkyl radical may likewise be employed.

With respect to the protolytic decomposition by water or by alcohols, this stability of the complex depends on the nature of the substitution of the ligand. However, this substitution can readily be tested in the environment, and for that purpose as a yardstick compound tris(perfluoroallyl)Rh is employed to establish the minimum activity vis-a-vis any other ligand usefully employable in this process. Another benchmark minimum activity compound is (perfluoroallyl)$_2$Rh(R), where R may be a more active ligand such as alkyl, or alkenyl or allyl.

For purposes of this invention, therefore, complexes which are reasonably stable to protonation by water or by alcohol and are stabilized such as by a trialkyl ammonium substituent present on an allylic radical may be employable and reasonably stable towards hydrolysis. However, these compounds may still be susceptible to protonation by the stronger (pK$_a$) acid in the zeolite cavity. Therefore, again, the protonation by the acid in the zeolite cavity, such as the acidified or pretreated zeolite as disclosed below, is the test by which the selection of the substituents or radicals on the metal complex are being made. On this basis, the protonation by the stronger acid in the zeolite cavity, in the formation of the appropriate [zeolite]—O—M—R reaction taking place, is the overriding consideration for the stability and/or employment of the suitable metal complexes. Along the same lines, enolates or enolate complexes can be employed. For example, an enolate of acetaldehyde or acetone and rhodium (III) is within the contemplation of the invention.

Similarly, enamine complexes may serve in an analogous manner and are within the contemplation of the invention, e.g. tris(dimethylamino ethene)Rh$^{+3}$.

For the sake of easy definition, the compounds herein have been defined as "grease balls." These are, by definition, an organo-metallic species in which ligands occupy all of the available (or non-reversibly-bound) coordination sites of the metal in which the exterior of the ligand (that face of the ligand presented to the solvent medium) is such that the complex presents itself to the solvent as a hydrocarbon, thus affording solubility in organic solvents, and confers the easy introduction of the complex into the apertures and cavities of the zeolite.

By the term "solubilized grease ball" is meant a "grease ball" such as defined above in which some substituents exist on the organic ligand, be it allylic, enolate or enamine, as discussed above, and which impart special solubility to the organo-metallic complex in the desired solvent medium and yet is capable of and susceptible to protonation by the stronger acid in the zeolite pore or cavity.

Thus by the above definitions it is pointed out that the herein defined invention depends on the fact that the loss of ligand occurs in the response to protonation only and that the acid site furnishing this protonation be strong enough to attack the complex used, but only in the apertures or within the zeolite cavity. Thus the support-substrate interaction in these cases is site-specific in that the transition metal will be bound only to that oxygen bearing the acidic proton. This is in contrast to a non-specific support-substrate interaction which would occur of a lone electron pair of, for example, an oxygen in a more or less random way. By the substrate is meant the introduced material to be reacted with the support. Still further and more importantly, it should be remembered that as a means for eliminating any residual lone electron pair or random reaction which may have occurred, there exist catalyst poisons which are of a size incapable of entering into the aperture or cavity of the zeolite to render innocuous the metal reacted with the strong acid site, but which by the size of the molecule can "clean up" the exterior of the zeolite and thus prevent any side reactions to occur. Representative compounds are dialkyl sulfides or trialkylamines or trialkylphosphines where the alkyl group is butyl or larger.

It is contemplated, however, that these random site substitutions under given circumstances may act on a mixture in a reaction stream in some beneficial manner, and for that reason the exterior substitution with larger molecules than capable of entering the apertures and cavities is recognized and is within the comtemplation of this invention.

Although the above discussion has been with respect to mono-metal systems, equally within the scope of the invention are bi-metal systems such as where the metal of one type is reacted in the apertures and cavities of the zeolite and a metal of another type is reacted on the exterior of the zeolite structure. Still further, inasmuch as from the present knowledge in each zeolite type X and Y catalyst system, at least two metal atoms can be reacted in the super cage, e.g. two rhodium species per super cage, it is within the contemplation of this invention that a mixed reactant stream may statistically be distributed within the super cage and thus different metals may react with the hydroxyl groups in the super cage.

Although the examples which are to follow herein illustrate the process being carried out by a batch process, other types of reactors are also within the contemplation of this invention, such as continuous flow reactors whereby the formation of by-products is mediated or eliminated. As one of the by-products in the reaction of carbonylation of methanol in the presence of methyl iodide, e.g. dimethyl ether is present. In a flow reactor its formation is less troublesome. As an example, the effect of this by-product can thus be further minimized and thus the selectivity of these carbonylation reactions improved.

Amongst the various continuous flow reactors are intended the pipe reactors, the turbulence generating reactors, etc., well known to those skilled in the art.

In the examples which are to follow, the various reactions are illustrated as well as the data showing the obtained product. These reactions show the products, confirm the specificity of product, and verify the comparable reaction rates with the non-zeolite supported metals.

Further, products which are obtained, yields and the explanation of the various analytical techniques for establishing the placement of the metal are set forth.

Although the examples which are to follow illustrate various facets of the invention, these are not to be construed as limiting the broader scope of the invention.

GENERAL EXAMPLE A

Standard Procedure for Zeolite Pretreatment

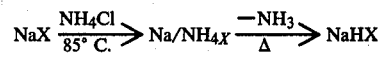

The sodium cations in the Linde 13X molecular sieve zeolite* (10 g) were replaced by ammonium cations by treatment of the sodium sieve with aqueous ammonium chloride for 48 hours with constant mechanical stirring. After filtration and washing several times with distilled water, the solid was dried at room temperature. To determine percent exchange of sodium cations, purified argon was passed over the sample at 350° C., then through a standard HCl solution. After 6 hours the ammonia absorbed was determined by titrating excess HCl with sodium hydroxide using methyl orange as indicator. To determine the protons in the deammoniated zeolite, the solid was evacuated under high vacuum ($10^{-6}$ mm Hg) at 250° C. for 3 hours. The dried solid was then titrated with methyllithium in tetrahydrofuran. The $CH_4$ gas evolved was quantified by using Toepler pump analysis. Both the results of ion exchange and titration are shown as follows:

| $NH_4Cl$, 8/g NaX | percent exchange | no. of cations exchanged per unit cell |
|---|---|---|
| 0.5 | 22% | 18 |
| Titration ot NaHX with MeLi | percent of protons** | no. of protons per unit cell |
| | 15% | 14 |

*This zeolite is described in "Linde Molecular Sieves - Absorbent Catalysts", Brochure F-1979B, e.g. on page 11 thereof, and "Linde Molecular Sieve Type 13X", Brochure F-23.
**The incomplete exchange may be attributable to the technique which was employed.

IR data for partially decationated 13X zeolite NaHX:
3750 cm$^{-1}$ (weak)
3650 cm$^{-1}$ (medium)
3550 cm$^{-1}$ (medium)

In a similar manner as above, Linde Type 10X molecular sieve may be treated. This material is also defined in the first-mentioned Brochure F-1979B and has a nominal pore diameter of 8 Angstroms; the other suitable molecular sieves can also be treated as illustrated in the previously mentioned article by Bolton, "Molecular Sieve Zeolites."

GENERAL EXAMPLE B

Deposition of the Rh Complex on NaHX

Reaction: (a)

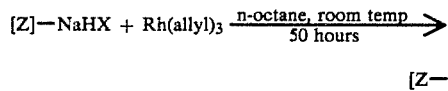

[Z]—NaHX + Rh(allyl)₃ $\xrightarrow[\text{50 hours}]{\text{n-octane, room temp}}$ [Z—X]—ORh(allyl)₂

Reagents:  
Zeolite-(NaHX): 1.6 g  
Rh(allyl)₃: 85 mg (0.38 mmol)  
n-octane: 25 mL

Procedure

To a 100-mL 3-necked round-bottomed flask equipped with a high-vacuum stopcock and 25 mL addition funnel was added pretreated zeolite-(NaHX). A 2% (w/v) weight by volume (on basis for zeolite as exchanged and pretreated as above) slurry was then prepared by adding 20 mL of freshly distilled n-octane. To the addition funnel was added an n-octane solution (5 mL) of Rh(allyl)₃. The Rh(allyl)₃ solution was added dropwise to the zeolite slurry. After the addition was complete, the mixture was stirred an additional 50 hours. After 50 hours volatiles of the reaction were completely removed in vacuo ($10^{-6}$ mm Hg) through a $-90°$ C. trap followed by a $-196°$ C. trap, thus separating propylene from n-octane solvent. The evolved gas was quantified in the calibrated PV manometer/trap to yield propylene (0.35 mmol, 0.92 equiv/equiv Rh(allyl)₃) verified by GC/MS (gas chromatograph/mass spectrometer) analysis (0.19% picric acid on Carbopack C, 6 M×2 mm, glass, 50° C.).

IR data: 3055, 2950-2800, 1490 cm$^{-1}$.

Reaction: (b)

Preparation of [Z—X]—ORh(allyl)H

[Z—X]—ORh(allyl)₂ + H₂ $\xrightarrow[\text{48 hours}]{\text{room temp.}}$

[Z—X]—ORh(allyl)H + C₃H₈ + C₆H₁₄

Reagents: [Z—X]—ORh(allyl)₂ 1.6 g (0.35 mmol Rh)  
H₂  1 atm

Procedure

To a 100-mL Schlenk flask equipped with a high-vacuum stopcock was added [Z—X]—ORh(allyl)₂, and the apparatus was attached to a high-vacuum line. The reaction was commenced by introducing H₂ into the Schlenk flask. After 2 hours the bulk material became dark gray. The reaction was allowed to stand for 2 days, after which time the hydrogen was evacuated. The reaction produced propane (0.22 mmol, 0.62 equiv/equiv Rh) and hexane (0.05 mmol, 0.14 equiv/equiv Rh) by GC analysis (total (C₃)=0.90 equiv/equiv Rh) (0.19% picric acid on Carbopack C, 6 M×2 mm, glass). The solid remaining was dark gray in color and was formulated as [Z—X]—ORh(allyl)H.

IR data: 3060, 2950-2800, 2010, 1490 cm$^{-1}$.

Reaction: (c)

Preparation of [Z—X]—ORhH₂

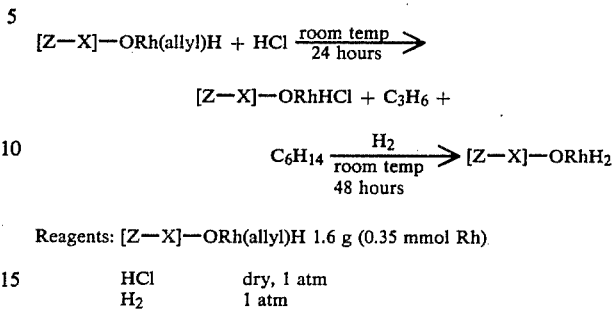

[Z—X]—ORh(allyl)H + HCl $\xrightarrow[\text{24 hours}]{\text{room temp}}$

[Z—X]—ORhHCl + C₃H₆ +

C₆H₁₄ $\xrightarrow[\text{48 hours}]{\text{H}_2\text{ room temp}}$ [Z—X]—ORhH₂

Reagents: [Z—X]—ORh(allyl)H 1.6 g (0.35 mmol Rh)  
HCl  dry, 1 atm  
H₂  1 atm

Procedure

To a 100-mL Schlenk flask was added [Z—X]—ORh(allyl)H. Then gaseous HCl was introduced at a pressure of 1 atm and the reaction was left to stand for one day to give dark brown [Z—X]—ORhHCl. The volatiles were isolated in vacuo ($10^{-6}$ mm Hg) by distillation into a $-196°$ C. trap after passage through KOH. The water was separated from organic volatiles by a second distillation. GC and GC/MS analysis found propylene (0.12 mmol, 0.34 equiv/equiv Rh), propane (0.16 mmol, 0.46 equiv/equiv Rh) and hexane (0.02 mmol, 0.06 equiv/equiv Rh). To the remaining [Z—X]—ORhHCl in the Schlenk flask was added hydrogen to a pressure of 1 atm. The reaction was left to stand for 2 days. The hydrogen was then removed by vacuum to give the dark brown dihydride, [Z—X]—ORhH₂.

IR data: For [Z—X]—ORhH₂, 2098, 2029 cm$^{-1}$.

Reaction: (d)

Preparation of [Z—X]—Rh(CO)₂

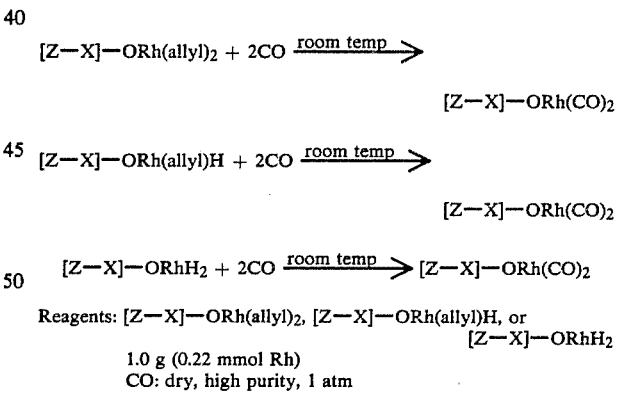

[Z—X]—ORh(allyl)₂ + 2CO $\xrightarrow{\text{room temp}}$

[Z—X]—ORh(CO)₂

[Z—X]—ORh(allyl)H + 2CO $\xrightarrow{\text{room temp}}$

[Z—X]—ORh(CO)₂

[Z—X]—ORhH₂ + 2CO $\xrightarrow{\text{room temp}}$ [Z—X]—ORh(CO)₂

Reagents: [Z—X]—ORh(allyl)₂, [Z—X]—ORh(allyl)H, or [Z—X]—ORhH₂  
1.0 g (0.22 mmol Rh)  
CO: dry, high purity, 1 atm

Procedure

[Z—X]—ORh(allyl)₂, [Z—X]—ORh(allyl)H, or [Z—X]—ORhH₂ were placed in a 100-mL Schlenk flask. The flask was attached to the high-vacuum line and the system was evacuated at room temperature for 1 hour. Carbon monoxide was then introduced to the Schlenk flask at 1 atm. The solid bulk in the flask was kept under CO atmosphere for 30 min. CO gas was then pumped off the system through a cold trap ($-196°$ C.). The organic volatiles were analyzed by GC/MS analysis. The solid bulk remaining was supported rhodium dicarbonyl.

IR data: For [Z—X]—Rh(CO)$_2$, 2094 cm$^{-1}$, 2025 cm$^{-1}$.

GENERAL EXAMPLE C

The following reactions provide information of the location of the rhodium complex on the zeolite support:

Reaction (1)—Olefinic Double-Bond Hydrogenation

Catalytic hydrogenations of olefins were performed in a flask equipped with a Teflon stopcock, sidearm and Teflon-coated spinbar magnet. The stirring rate was held constant at the maximum attainable rate for all reactions to insure equivalent hydrogent diffusion. The flask was attached to a constant-pressure (1 atm) mercury buret manifold; the rate of hydrogenation was determined by monitoring the rise of the mercury column in the buret as H$_2$ was reacted. The mercury bulb was leveled so that the pressure in the system was always 1 atm.

Olefins studied were 2-butene, 1-hexene, 1-octene, 2-methyl-2-butene, 2,3-dimethyl-2-butene, cyclohexene, cyclopentene, 1-methyl-1-cyclohexene, 3-methyl-1-cyclohexene, methylenecyclohexane, cycloheptene, cyclooctene, 1-methylcyclopentene.

When [Z—X]—ORh(allyl)H was employed as a catalyst, linear uptake of H$_2$ was observed for all olefins. The rate was found to have a significant dependence on the size of the olefinic substrates. The results are illustrated in FIG. 1.

The conditions for the reactions depicted in FIG. 1 were: [Z—X]—ORh(allyl)H (50 mg, 0.01 mmol Rh); [olefin]=0.2 M in hexane; H$_2$ (1 atm); 20° C.

The results, as shown in FIG. 1, confirm that the rhodium catalyst stays in the super cage of the zeolite so that only those olefinic substrates which can penetrate through the channel can be hydrogenated.

A further experiment verifies the above conclusion. During the hydrogenation of 1-butene, both P(n-Bu)$_3$ and PMe$_3$ were sequentially added to the reaction. From the results shown in FIG. 2 it is revealed that the addition of P(n-Bu)$_3$ did not change the turnover rate. However, the addition of PMe$_3$ almost immediately poisoned the catalyst. P(n-Bu)$_3$ is sufficiently large so that it cannot go through the zeolite channel to coordinate the rhodium complex; however, PMe$_3$ can easily penetrate into the super cage and poison the active catalytic species. The above procedure may also be used for "cleaning up" the exterior of the zeolite of any stray metal reactants.

GENERAL EXAMPLE D

The following infrared spectroscopic studies of [Z—X]—ORh(allyl)H, after in situ treatments with CO, MeI and MeOH individually or in mixtures under static conditions, provide evidence about rhodium-complex formation in the methanol carbonylation reactions:

The IR pellets made of [Z—X]—ORh(allyl)H were placed in an evacuable infrared cell made of stainless steel and fitted with NaCl windows. The cell was connected to a vacuum manifold for exposing the zeolite to known subatmospheric pressures of reactants.

Possible assignments of the absorption bands of the reaction species were made according to the following scheme:

3055 cm$^{-1}$
2950–2800 cm$^{-1}$
1490 cm$^{-1}$
2010 cm$^{-1}$

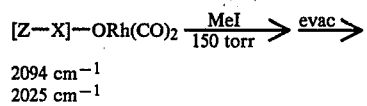

2094 cm$^{-1}$
2025 cm$^{-1}$

[Z—X]—ORh(CO)(COCH$_3$)(I)

2071 cm$^{-1}$
2002 sh
1724 cm$^{-1}$

GENERAL EXAMPLE E

Preparation of [Z—Y]—ORh(allyl)$_2$, [Z—Y]—ORh(allyl)H and [Z—Y]—ORh(CO)$_2$

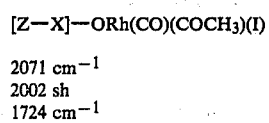

(NaY: Type SK-40 from Union Carbide, Linde.)

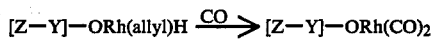

Procedure

The same procedures as those described for the analogues of X-type zeolite supports are used to prepare zeolite (Y type)-supported rhodium complexes.

From calibration it is found that there is 2%, w/w Rh deposited on zeolite (Y type).

GENERAL EXAMPLE F

Preparation of [Si]—ORh(allyl)$_2$, [Si]—ORh(allyl)H and [Si]—ORhH$_2$

As Silica, Aerosil 300, at 300 m$^2$/g, available from Degussa Corp., was used.

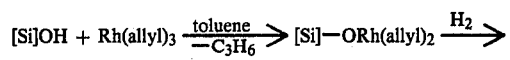

SiO$_2$ for purposes of this description is illustrated as [Si]OH to show the presence of —OH groups.

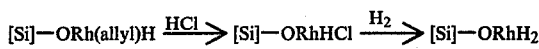

Procedure

The same procedure as those described for the analogues of zeolite supports are used to prepare the silica-supported rhodium complexes.

From calibration it is found that there is 4% w/w percentage Rh deposited on silica.

GENERAL EXAMPLE G

Preparation of [Al]—ORh(allyl)$_2$ and [Al]OH—ORhH$_2$

As alumina, aluminum oxide C from Degussa Corp. was used.

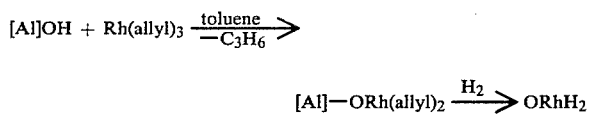

Al$_2$O$_3$ for purposes of this description is illustrated as [Al]OH to show the presence of —OH groups.

Procedure

The same procedures as those described for the analogues of zeolite supports are used to prepare the alumina-supported rhodium complexes.

From calibrations it is found that there is 3% w/w percentage Rh deposited on aluminum oxide.

GENERAL EXAMPLE H

Preparation of [Z—X]Co(CO)n

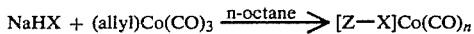

Procedure

The same procedure as those described for the analogues of zeolite supports are used to prepare zeolite-supported cobalt complexes.

From calibration the minimum percentage of cobalt deposited on zeolite is 1.5%.

IR for [Z—X]Co(CO)$_n$:1935 cm$^{-1}$, 1880 cm$^{-1}$.

The following specific examples are given for methanol carbonylation using [Z—X]—ORh(allyl)$_2$, [Z—X]—ORh(allyl)H, [Z—X]—ORhH$_2$, [Z—X]—ORh(CO)$_2$, [Si]—ORh(allyl)H, [Al]—ORhH$_2$ or [Z—Y]—ORh(allyl)$_2$ as catalysts.

EXAMPLE 1

A batch reactor is charged with the following ingredients: 50 mg of [Z—X]—ORh(allyl)H (0.01 mmol Rh), 0.6 grams (4.8 mmol) of methyl iodide, 12 grams (15 mL, 0.37 mol) of methanol.

The reactor is pressurized with carbon monoxide to a total pressure of 1000 psig. Then the reactor is heated to 200° C. The reaction is carried out at a constant pressure to yield a solution containing the following distribution of products:

| | |
|---|---|
| dimethyl ether | 8% |
| acetic acid | 6% |
| methyl acetate | 59% |
| methyl iodide | 1% |
| methanol, water, catalyst | 26% |

The time required for the above conversion of methanol to methyl acetate is 10 hours. Therefore, the turnover rate is 1090 mol AcOMe/mol Rh/hour.

$$\text{Selectivity: } \frac{[AcOH] + 2[AcOMe]}{2X[MeOMe] + [AcOH] + 2X[AcOMe]} = 89\%$$

EXAMPLE 2

A batch reactor is charged with the following ingredients: 50 mg of [Z—X]—ORh(allyl)H (0.01 mmol Rh), 1.14 grams (8 mmol) of methyl iodide, 8 grams (10 mL, 0.25 mol) of methanol.

The reactor is pressurized with carbon monoxide to a total pressure of 500 psig. Then the reactor is heated to 180° C. The reaction is carried out a constant pressure to yield a solution containing the following distribution of products:

| | |
|---|---|
| dimethyl ether | 8% |
| methyl acetate | 41% |
| acetic acid | 3% |
| methyl iodide | 1% |
| methanol, catalyst, water | 47% |
| Selectivity: | 84% |

The time required for the above conversion is 10 hours. Therefore, the turnover rate is 336 mol AcOMe/mol Rh/hour.

EXAMPLE 3

A batch reactor is charged with the following ingredients: 50 mg of [Z—X]—ORhH$_2$ (0.01 mmol Rh), 1.0 gram (5.6 mmol) of methyl iodide, 12 grams (15 mL, 0.37 mol) of methanol.

The reactor is pressurized with carbon monoxide to a total pressure of 1000 psig. Then the reactor is heated to 190° C. The reaction is carried out at a constant pressure to yield a solution containing the following distribution of products:

| | |
|---|---|
| dimethyl ether | 10% |
| acetic acid | 3% |
| methyl acetate | 48% |
| catalyst, methanol, etc. | 39% |
| Selectivity: | 81% |

The time required for the above conversion is 10 hours. Therefore, the turnover rate is 680 mol acetate/mol Rh/hour.

EXAMPLE 4

A batch reactor is charged with the following ingredients: 50 mg of [Z—X]—ORh(allyl)H (0.01 mmol Rh), 5 mL of aqueous 47% HI solution, 12 grams (15 mL, 0.37 mol) of methanol.

The reactor is pressurized with carbon monixide to a total pressure of 1000 psig. Then the reactor is heated to 175° C. The reaction is carried out at a constant pressure to yield a solution containing the following distribution of products:

| | |
|---|---|
| dimethyl ether | 34% |
| methyl acetate | 16% |
| acetic acid | <1% |
| catalyst, methanol, etc. | 49% |
| Selectivity: | 33% |

The time required for the bove conversion is 10 hours. Therefore, the turnover rate is 240 mol acetate/mol Rh/hour.

EXAMPLE 5

A batch reactor is charged with the following ingredients: 50 mg of [Z—X]—ORh(allyl)H (0.01 mmol Rh), 0.6 grams (4.8 mmol) of methyl iodide and 8 grams (10 mL, 0.25 mol) of methanol. The reactor is pressurized with a mixture of carbon monoxide and hydrogen (CO to $H_2$ ratio is 9:1) to a total pressure of 500 psig. Then the reactor is heated to 200° C. After the reaction the product distribution is as follows:

| | |
|---|---|
| dimethyl ether | 8% |
| methyl acetate | 30% |
| acetic acid | 2% |
| methanol, catalyst, etc. | 60% |
| Selectivity: | 80% |

The time required for the above conversion is 15 hours. Therefore, the turnover rate is 127 mol actate/mol Rh/hour.

EXAMPLE 6

A batch reactor is charged with the following ingredients: 50 mg of [Z—X]—ORh(allyl)$_2$ (0.01 mmol Rh), 0.6 grams (4.8 mmol) of methyl iodide, 12 grams (15 mL, 0.37 mol) of methanol.

The reactor is pressurized with carbon monoxide to a total pressure of 1000 psig. Then the reactor is heated to 180° C. The reaction is carried out at a constant pressure to yield a solution containing the following distribution of products:

| | |
|---|---|
| dimethyl ether | 8% |
| acetic acid | 7% |
| methyl acetate | 45% |
| methyl iodide, methanol, catalyst, etc. | 40% |
| Selectivity: | 86% |

The time required for the above conversion of methanol to methyl acetate is 10 hours. Therefore, the turnover rate is 560 mol acetate/mol Rh/hour. The rate has changed in this Example in contrast from Examples 1 and 3 because of the change in temperature in each reaction.

EXAMPLE 7

A batch reactor is charged with the following ingredients: 50 mg of [Z—X]—ORh(CO)$_2$ (0.01 mmol Rh), 0.8 gram (5 mmol) of methyl iodide, 8 grams (0.25 mol) of methanol.

The reactor is pressurized with carbon monoxide to a total pressure of 500 psig. Then the reactor is heated to 180° C. The reaction is carried out at a constant pressure to yield a solution containing the following distribution of products:

| | |
|---|---|
| dimethyl ether | 7% |
| acetic acid | 5% |
| methyl acetate | 42% |
| methanol, water, catalyst, etc. | 46% |
| Selectivity: | 86% |

The time required for the above conversion is 10 hours. Therefore, the turnover rate is 530 mol acetate/mol Rh/hour.

EXAMPLE 8

A batch reactor is charged with the following ingredients: 50 mg of [Al]—ORhH$_2$ (0.015 mmol Rh), 0.8 grams (5 mmol) of methyl iodide, 12 grams (15 mL, 0.37 mol) of methanol.

The reactor is pressurized with carbon monoxide to a total pressure of 1000 psig. Then the reactor is heated to 180° C. The reaction is carried out at a constant pressure to yield a solution containing the following distribution of products:

| | |
|---|---|
| dimethyl ether | 18% |
| acetic acid | 2% |
| methyl acetate | 15% |
| methanol, water, catalyst, etc. | 65% |
| Selectivity: | 47% |

The time required for the above conversion is 10 hours. Therefore, the turnover rate is 121 mol AcOMe/mol Rh/hour.

EXAMPLE 9

A batch reactor is charged with the following ingredients: 50 mg of [Z—Y]—ORh(allyl)$_2$ (0.01 mmol Rh), 0.8 grams (5 mmol) of methyl iodide, 12 grams (15 mL, 0.37 mol) of methanol.

The reactor is pressurized with carbon monoxide to a total pressure of 500 psig. Then the reactor is heated to 180° C. The reaction is carried out at a constant pressure to yield a solution containing the following distribution of products:

| | |
|---|---|
| dimethyl ether | 8% |
| methyl acetate | 38% |
| acetic acid | 3% |
| methanol, water, catalyst, etc. | 51% |
| Selectivity: | 83% |

The time required for the above conversion is 8 hours. Therefore, the turnover rate is 385 mol AcOMe/mol Rh/hour.

EXAMPLE 10

A batch reactor is charged with the following ingredients: 30 mg of [Si]—ORh(allyl)H (0.01 mmol Rh), 0.8 grams (5.6 mmol) of methyl iodide, 12 grams (0.37 mol) of methanol.

The reactor is pressurized with carbon monoxide to a total pressure of 500 psig. Then the reactor is heated to 200° C. The reaction is carried out at a constant pressure to yield a solution containing the following distribution of products:

| | |
|---|---|
| dimethyl ether | 15% |
| methyl acetate | 16% |
| methanol, water, catalyst, etc. | 69% |
| Selectivity: | 52% |

The time required for the above conversion is 10 hours. Therefore, the turnover rate is 133 mol AcOMe/mol Rh/hour.

EXAMPLE 11

A batch reactor is charged with the following ingredients: 200 mg of [Z—X]Co(CO)$_n$ (0.05 mmol Co), 1.0 grams (5.6 mmol) of methyl iodide, 12 grams (0.37 mol) of methanol.

The reactor is pressurized with carbon monoxide to a total pressure of 1000 psig. Then the reactor is heated to 200° C. The reaction is carried out at a constant pressure to yield a solution containing the following distribution of products:

| | |
|---|---|
| dimethyl ether | 48% |
| acetic acid | 8% |
| methyl acetate | 9% |
| methanol, water, methyl iodide, etc. | 35% |
| Selectivity: | 22% |

The time required for the above conversion of methanol to methyl acetate is 30 hours. Therefore, the turnover rate is 65 mol AcOMe/mol Co/hour.

EXAMPLE 12

A batch reactor is charged with the following ingredients: [Z—X]—ORh(CO)$_2$, 50 mg (0.01 mmol Rh); methyl chloride, 10 mmol; methanol, 10 mL.

The reactor is pressurized with carbon monoxide to a total pressure of 1000 psig. Then the reactor is heated to 200° C. The reaction is carried out at a constant pressure to yield 6.38 mmol of methyl acetate after 20 h. The total conversion from methyl chloride to methyl acetate is 64%.

EXAMPLE 13

A batch reactor is charged with the following ingredients: [Al]—ORhH$_2$, 50 mg (0.015 mmol Rh); methyl chloride, 10 mmol; methanol, 10 mL.

The reactor is pressurized with carbon monoxide to a total pressure of 1000 psig. Then the reactor is heated to 200° C. The reaction is carried out a constant pressure to yield 4.2 mmol of methyl acetate after 20 h. The total conversion from methyl chloride to methyl acetate is therefore 42%.

EXAMPLE 14

Further use of the above-identified zeolite catalysts is convincingly demonstrated in applications such as Fischer-Tropsch synthesis. A brief summary of this method is described by Hagin, "Fischer-Tropsch: New Life for Old Technology", C&EN, (Oct. 26, 1981), pp. 22-32.

In accordance with this process two comparative reactions were run.

(a) A batch reactor, of a volume 300 ml is charged with the following ingredients: 150 mg [Al]—ORhH$_2$ (0.045 mmol Rh), 18 ml sulfolane, and 400 mg KI. The reactor is pressurized with CO (600 psi) and H$_2$ (600 psi) and is then heated to 230° for 20 h. The following distribution of products is obtained:

| | |
|---|---|
| propane | <10% |
| methyl iodide | <10% |
| butane | <10% |
| isomeric butenes | 3% |
| isomeric pentenes | <1% |
| pentadiene | 5% |
| pentane | 1% |
| isomeric hexenes | 40% |
| hexadiene | 3% |
| hexane | 38% |

Total weight of products is 0.7 gram. An approximate turnover rate of 55 mol CO/mol Rh/h is calculated.

(b) The same reaction performed using as catalyst [Z—X]—ORh(allyl)H proceeded extremely vigorously with outstanding results but in a runaway fashion. Lower pressure of CO and H$_2$ and control of reactor temperature gives a reaction which is exceptionally outstanding.

Example 14(a) above illustrates two points. One, the Fischer-Tropsch reaction is outstanding at these low pressures using alumina supported catalyst modified according to the novel method. The second point is the order of magnitude improvement achievable when employing zeolites "cage" catalysts when comparing the reactions (a) and (b) above.

From the above, it is demonstrated that the above-illustrated deposition methods can be implemented using partially proton-exchanged zeolites (preferably those with super cages > 10 Angstroms in diameter) and have demonstrated the selective entrapment of the transition metal species inside the super cage. Properties of oxide-bound catalyst species can thus be modified by entrapping the transition metal species within a zeolite cavity. Such modification derives from the "molecular sieve" property of the micro crystals and from the possibility that "three-dimensional" environmental aspects of the super cage can influence substrate-catalyst interactions.

Tris(allyl)rhodium reacts with surface hydroxyl groups (acid sites), particularly those located within the zeolite cavities of partially decationated X or Y type zeolites, under mild conditions, to form the supported bis(allyl)rhodium complex [Z—X]—ORh(allyl)$_2$, as shown by the following Illustration I.

Illustration I

Formation and Reactions of Zeolite-Supported Rhodium Hydrides

[Z] = Zeolite
[Z]—OH = Hydroxyl group inside the super cage

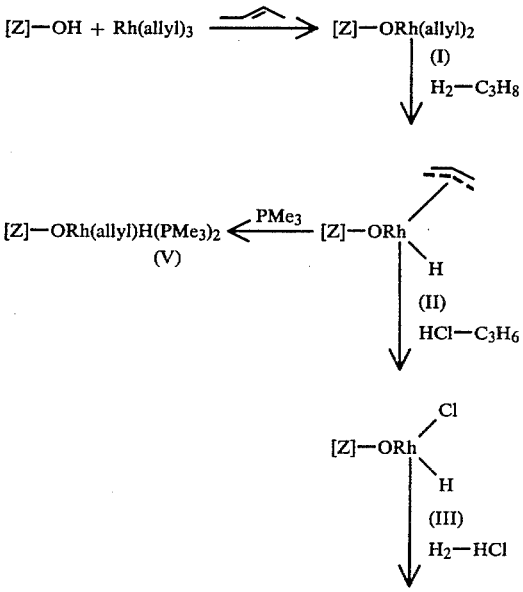

-continued

[Z]—ORh(H)₂(PMe₃)₂ (VI) $\xleftarrow{PMe_3}$ [Z]—ORh$\diagup^H_H$ (IV)

Propylene evolved during deposition was identified by GC/MS and was determined quantitatively using a calibrated PV manometer. It was found that 2 equiv rhodium are deposited per unit cell of the zeolite. Subsequent treatment of (I) with H₂ leads to the formation of zeolite-bound rhodium hydride (II) ($\nu$Rh—H=2010 cm$^{-1}$) with concommitant evolution of 1 equiv propane. In contrast to its silica-supported analogue, no bridging hydride ligands could be detected by IR; this suggests a distribution of mononuclear complexes in the zeolite cage. The remaining allylic group of (II) could be removed either via slow hydrogenolysis (>10 days) or by reaction with gaseous HCl (1 atm); this latter process yields propene (0.34 equiv), propane (0.46 equiv), and hexane (0.06 equiv). Zeolite-supported rhodium hydridochloride species (III) is also formed. Treating (III) with H₂ yields (IV); two Rh—H bands of equal intensity are observed by IR ($\nu$Rh—H=2098, 2029 cm$^{-1}$) which suggests that (IV) is a supported rhodium dihydride. No bridging hydride ligands could be detected.

Relative rates for hydrogenation of variously substituted olefins catalyzed by silica-supported rhodium hydrides depend solely on local steric congestion about the double bond.

In contrast, according to Illustration I, while (II) exhibits high catalytic activity for olefin hydrogenation, shape selectivity for the substrate (attributed to the "molecular sieve" nature of the zeolite support) is confirmed. Indeed, when (II) was employed as a catalyst, linear uptake of H₂ was observed in hydrogenation experiments for all olefins studied (cf. FIG. 1). However, rates for hydrogenation of olefinic substrates larger than cyclohexene were negligible, demonstrating that the catalytically reactive center is located within the intracrystalline volume of the zeolite. Therefore, transport restrictions preclude hydrogenation of molecules of shapes unable to pass through the crystalline channels. For example, whereas rates for 1-butene and 1-hexene hydrogenation are comparable using [Si-]—ORh(allyl)H, for (II) these rates decrease 1-butene>1-hexene>1-octene. Additionally, as expected, 1-butene (and expectedly 1-hexene or 1-octene) is hydrogenated more rapidly than is 2,3-dimethyl-2-butene using [Si]ORh(allyl)H; using zeolite-bound catalyst (II), however, limitations of transport are such that the locally high substituted but "small" 2,3-dimethyl-2-butene is hydrogenated more readily than is the "larger" long-chain primary olefin, 1-octene. Also consistent with this notion of shape selectivity is the observation that benzene can be efficiently hydrogenated to give cyclohexane (500 psi H₂, 120° C.) on [Z—X-]—O—Rh(allyl)H at an appreciable rate (203 turnovers per hour), but under the same conditions toluene is not hydrogenated at all.

The high activity of [Z—X]—ORh(CO)₂ compared with silica- or alumina-supported analogues may be attributed to a support-substrate interaction which exists inside the zeolite cage environment: departure of halide (in a displacement reaction) may be facilitated by interaction between the leaving group and Lewis acidic sites of the zeolite cage. From the above and in general, the reactants as otherwise unreactive toward carbonylation as methyl chloride, can now be readily carbonylated in the presence of methanol using rhodium complexes bound to Lewis acidic supports (for example, for [Al]—ORh(CO)₂; based on temperature, hours, pressure of CO, and turnover).

When discussing above the introduction of the metal complex in the zeolite pore, channel, aperture or cage, useful solvents are those in which the above described complexes are soluble yet are not reactive with the solvents. As typical solvents alkanes, especially straight chain alkanes, are preferred. For other supports, arenes, such as benzene, toluene, etc., can be employed. Solvent selection for the above purposes is well known in the art.

While the above illustrations are for the purpose of explaining and/or comparing the various activities of the support-rhodium and zeolite-rhodium catalysts, the same considerations also apply to the other metals which can be deposited within the zeolite. Further, while the theoretical explanations for the outstanding results are believed to be correct, these explanations are merely for the purpose of facilitating the understanding of the invention, and not to limit the scope of the invention which has been defined in the claims appended herein.

What is claimed is:

1. A process for preparation of a heterocatalyst system comprising the steps of: reacting at least one metal complex with an active —OH group of sufficient activity within a pore, aperture, channel, cage or cavity of a zeolite or molecular sieve, said metal complex being of a size capable of entering said pore, aperture, channel, cage or cavity of said zeolite or molecular sieve and reacting with an —OH group therein; forming of at least one metal—O—zeolite or metal—O—molecular sieve bond with said complex in said pore, aperture, channel, cage or cavity of said zeolite or molecular sieve, and recovering said reaction product of metal—O—zeolite or metal—O—molecular sieve as a catalyst.

2. The process as defined in claim 1 wherein the metal complex is in a solvent solution and is of a size less than about 10 Angstroms and is capable of entering said pore, aperture, channel, cage or cavity of said zeolite and reacting therewith with a sufficiently acidic —OH group.

3. The process as defined in claim 1 wherein the complex is substituted with an alkyl, allyl, alkenyl, alkynyl or aryl group, or mixtures of these groups, of 2 to 8 carbon atoms corresponding in number to the metal in its oxidation states.

4. The process as claimed in claim 1 wherein the complex is further substituted with a neutral ligand.

5. The process as defined in claim 3 wherein the complex is a metal substituted with allylic groups corresponding in number to the metal in its oxidation states.

6. The process as defined in claim 3 wherein the complex is of rhodium.

7. The process as defined in claim 5 wherein the complex is of cobalt.

8. The process as defined in claim 1 wherein the complex is of a Group VIII metal.

9. The process as defined in claim 8 wherein the complex is a cobalt complex.

10. The process as defined in claim 1 wherein the zeolite is a type X or Y zeolite or molecular sieve containing an —OH group within said pore, aperture, channel, cage or cavity of the same.

11. The process as defined in claim 1 which comprises reacting a protolytically labile metal complex and an active —OH group of a zeolite or a molecular sieve wherein the active —OH group is within a pore, aperture, channel, cage or cavity of said zeolite or molecular sieve.

12. The process as defined in claim 11 wherein the zeolite is a type X or Y zeolite.

13. The process as defined in claim 1 wherein the molecular sieve is type Omega molecular sieve.

14. The process as defined in claim 1 wherein the molecular sieve is a mordenite, type L, erionite or crystalline silicalite having uniform pore dimensions of at least about 5 Angstroms.

15. The process as defined in claim 12 wherein a rhodium complex is reacted with the zeolite.

16. The process as defined in claim 12 wherein a cobalt complex is reacted with said zeolite.

17. The process as defined in claim 14 wherein a rhodium complex is reacted with said molecular sieve.

18. The process as defined in claim 14 wherein a cobalt complex is reacted with said molecular sieve.

19. The process as defined in claim 1 wherein after the reaction with said —OH group of said zeolite or molecular sieve said metal complex reaction product therewith is partially hydrogenated.

20. The process as defined in claim 1 wherein after the reaction with said —OH group of said zeolite or molecular sieve said metal complex reaction product therewith is further reacted with carbon monoxide.

21. The process as defined in claim 19 wherein a partial hydrogenation product thereof is further reacted with carbon monoxide.

22. The process as defined in claim 1 wherein after the reaction with said —OH group of said zeolite or molecular sieve said metal complex reaction product therewith is reacted with a poison for said metal complex of a size incapable of entering said pore, aperture, channel, cage or cavity of said zeolite or said molecular sieve.

23. The process as defined in claim 1 wherein said zeolite or molecular sieve is first pretreated by protonation of the same before said zeolite or molecular sieve is reacted with said metal complex.

24. The process as defined in claim 1 wherein one complex of one metal and another complex of another metal is reacted with at least two —OH groups of said zeolite or molecular sieve.

25. The process as defined in claim 24 wherein both metal complexes are within said pore, aperture, channel, cage or cavity of said zeolite molecular sieve.

26. The process as defined in claim 24 wherein one of said metal complexes is within said pore, aperture, channel, cage or cavity and the other is on the exterior of said zeolite or molecular sieve.

27. The process as defined in claim 1 wherein a complex capable of reaction with said zeolite or molecular sieve is tris(perfluoroallyl)rhodium, and the zeolite or molecular sieve is type 13X or 13Y.

28. A heterocatalyst comprising at least one metal complex reaction product with a zeolite or molecular sieve —OH group wherein the metal complex reaction product with said —OH group is within the pores, apertures, channels, cage, or cavity of said zeolite or molecular sieve.

29. The heterocatalyst as defined in claim 28 wherein said metal complex reaction product with said zeolite or molecular sieve is a partially hydrogenated or hydrated product of rhodium.

30. The heterocatalyst as defined in claim 28 wherein the metal complex reaction product with said zeolite or molecular sieve is a metal carbonyl.

31. The heterocatalyst as defined in claim 28 wherein the metal complex is a Group VIII metal.

32. The heterocatalyst as defined in claim 31 wherein the metal complex reaction product with said zeolite or molecular sieve is a reaction product of a rhodium complex.

33. The heterocatalyst as defined in claim 32 wherein the reaction product is a hydrated rhodium derived from tris(allyl)rhodium.

34. The heterocatalyst as defined in claim 33 wherein the reaction product is partially hydrogenated.

35. The heterocatalyst as defined in claim 28 wherein the zeolite is type X and Y zeolite.

36. The heterocatalyst as defined in claim 35 wherein the metal complex reaction product is with type X and Y zeolite and the metal complex is of a Group VIII metal complex.

37. The heterocatalyst as defined in claim 36 wherein the Group VIII metal is cobalt, nickel, rhodium, palladium, platinum or mixtures of same.

38. The heterocatalyst as defined in claim 36 wherein the Group VIII metal is rhodium.

39. The heterocatalyst as defined in claim 36 wherein the Group VIII metal is cobalt.

40. The heterocatalyst as defined in claim 36 wherein the Group VIII metal is a mixture of two metals.

41. A heterocatalyst of a type X or Y zeolite and a reaction product with a rhodium complex or rhodium carbonyl wherein said rhodium reaction product or rhodium carbonyl is within a pore, aperture, or cage of said zeolite.

42. A heterocatalyst of

[Z]—O—Rh(allyl)$_2$; [Z]—O—Rh—(allyl)H;

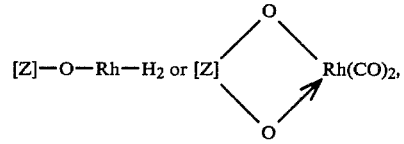

wherein [Z]— is a zeolite or a molecular sieve and wherein the —O— group of the [Z]—O— group is within a pore, aperture, channel, cavity or cage of said zeolite or molecular sieve.

43. The heterocatalyst as defined in claim 42 wherein the zeolite is an acidified type X zeolite.

44. The heterocatalyst as defined in claim 42 wherein the zeolite is an acidified type Y zeolite.

45. The heterocatalyst as defined in claim 42 wherein the molecular sieve is a type L, Omega or silicalite molecular sieve.

* * * * *